(12) United States Patent
Sumiya

(10) Patent No.: US 8,246,169 B2
(45) Date of Patent: Aug. 21, 2012

(54) OPHTHALMIC IMAGING APPARATUS

(75) Inventor: Toshifumi Sumiya, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 371 days.

(21) Appl. No.: 12/709,983

(22) Filed: Feb. 22, 2010

(65) Prior Publication Data

US 2010/0220287 A1   Sep. 2, 2010

(30) Foreign Application Priority Data

Mar. 2, 2009 (JP) .................................. 2009-048508

(51) Int. Cl.
  *A61B 3/10* (2006.01)
  *A61B 3/14* (2006.01)
(52) U.S. Cl. ......... 351/206; 351/205; 351/214; 351/221
(58) Field of Classification Search .................. 351/205, 351/206, 214, 221
  See application file for complete search history.

(56) References Cited

U.S. PATENT DOCUMENTS

| | | | |
|---|---|---|---|
| 6,099,127 | A | 8/2000 | Manivannan et al. |
| 6,618,531 | B1 | 9/2003 | Goto et al. |
| 7,306,336 | B2 | 12/2007 | Akita et al. |
| 7,484,849 | B2 | 2/2009 | Akita et al. |
| 2006/0051037 | A1 | 3/2006 | Goto et al. |

FOREIGN PATENT DOCUMENTS

| | | |
|---|---|---|
| JP | A-7-136127 | 5/1995 |
| JP | A-2000-105394 | 4/2000 |
| JP | A-2000-517227 | 12/2000 |
| JP | A-2004-61801 | 2/2004 |
| JP | A-2005-051257 | 2/2005 |
| JP | A-2005-185590 | 7/2005 |
| JP | A-2008-80066 | 4/2008 |

*Primary Examiner* — Ricky Mack
*Assistant Examiner* — Mahidere Sahle
(74) *Attorney, Agent, or Firm* — Oliff & Berridge, PLC

(57) ABSTRACT

An ophthalmic imaging apparatus comprises: a laser emitter that includes an ultrashort pulse light source and emits a laser beam with a tunable wavelength in a predetermined visible wavelength range; an irradiation optical system that includes a scanner for scanning the laser beam two-dimensionally and irradiates the laser beam emitted from the laser emitter to a predetermined portion of an examinee's eye; a light receiving optical system including an apertured plate placed in a substantially conjugate position of a focal point of the laser beam on the predetermined portion and a light receiving element for receiving the laser beam reflected by the predetermined portion and passed through the apertured plate; a controller that controls the laser emitter to continuously change a central wavelength of the laser beam in a predetermined visible wavelength range and controls the scanner in association with the wavelength change of the laser beam to two-dimensionally change an irradiation position of the laser beam; a memory that stores a light reception signal of the light receiving element associated with the wavelength change of the laser beam and the irradiation position change of the laser beam; and a display, the controller being adapted to display an image of the predetermined portion on the display based on the light reception signal stored in the memory.

5 Claims, 3 Drawing Sheets

A: SPECTRAL DATA OBTAINING TIME
B: SPECTRAL DATA NON-OBTAINING TIME
C: REFLECTION ANGLE FIXED (FIRST IRRADIATION POSITION)
D: REFLECTION ANGLE FIXED (SECOND IRRADIATION POSITION)
E: REFLECTION ANGLE CHANGED
F: WAVELENGTH CHANGE
G: VISIBLE RANGE

OPHTHALMIC IMAGING APPARATUS

CROSS-REFERENCE TO RELATED APPLICATIONS

This application is based upon and claims the benefit of priority from the prior Japanese Patent Application No. 2009-48508 filed on Mar. 2, 2009, the entire contents of which are incorporated herein by reference.

TECHNICAL FIELD

The present invention relates to an ophthalmic imaging apparatus for obtaining a front image of a predetermined portion of an examinee's eye.

BACKGROUND ART

There is an known ophthalmic imaging apparatus arranged to scan a laser beam on a predetermined portion (a fundus, an anterior segment, etc.) of an examinee's eye and receive the laser beam reflected by the predetermined portion to thereby obtain a front image of the predetermined portion. Such apparatus is provided with for example two or more types of monochromatic laser sources such as an infrared laser source, a red laser source, a green laser source, a blue laser source, and others. These laser sources are selectively used according to purposes of medical examinations and so on.

However, the apparatus provided with two or more types of the monochromatic laser sources tends to have a complex structure. Furthermore, obtainable images are limited according to the types of the laser sources.

SUMMARY OF INVENTION

Technical Problem

The present invention has been made in view of the circumstances to solve the above problems and has a purpose to provide an ophthalmic imaging apparatus capable of appropriately obtaining a front image (a hyperspectral image or a multispectral image) of a predetermined portion of an examinee's eye.

Solution to Problem

To achieve the above purpose, the present invention provides an ophthalmic imaging apparatus comprising: a laser emitter that includes an ultrashort pulse light source and emits a laser beam with a tunable wavelength in a predetermined visible wavelength range; an irradiation optical system that includes a scanner for scanning the laser beam two-dimensionally and irradiates the laser beam emitted from the laser emitter to a predetermined portion of an examinee's eye; a light receiving optical system including an apertured plate placed in a substantially conjugate position of a focal point of the laser beam on the predetermined portion and a light receiving element for receiving the laser beam reflected by the predetermined portion and passed through the apertured plate; a controller that controls the laser emitter to continuously change a central wavelength of the laser beam in a predetermined visible wavelength range and controls the scanner in association with the wavelength change of the laser beam to two-dimensionally change an irradiation position of the laser beam; a memory that stores a light reception signal of the light receiving element associated with the wavelength change of the laser beam and the irradiation position change of the laser beam; and a display, the controller being adapted to display an image of the predetermined portion on the display based on the light reception signal stored in the memory.

DESCRIPTION OF EMBODIMENTS

Figure 1:
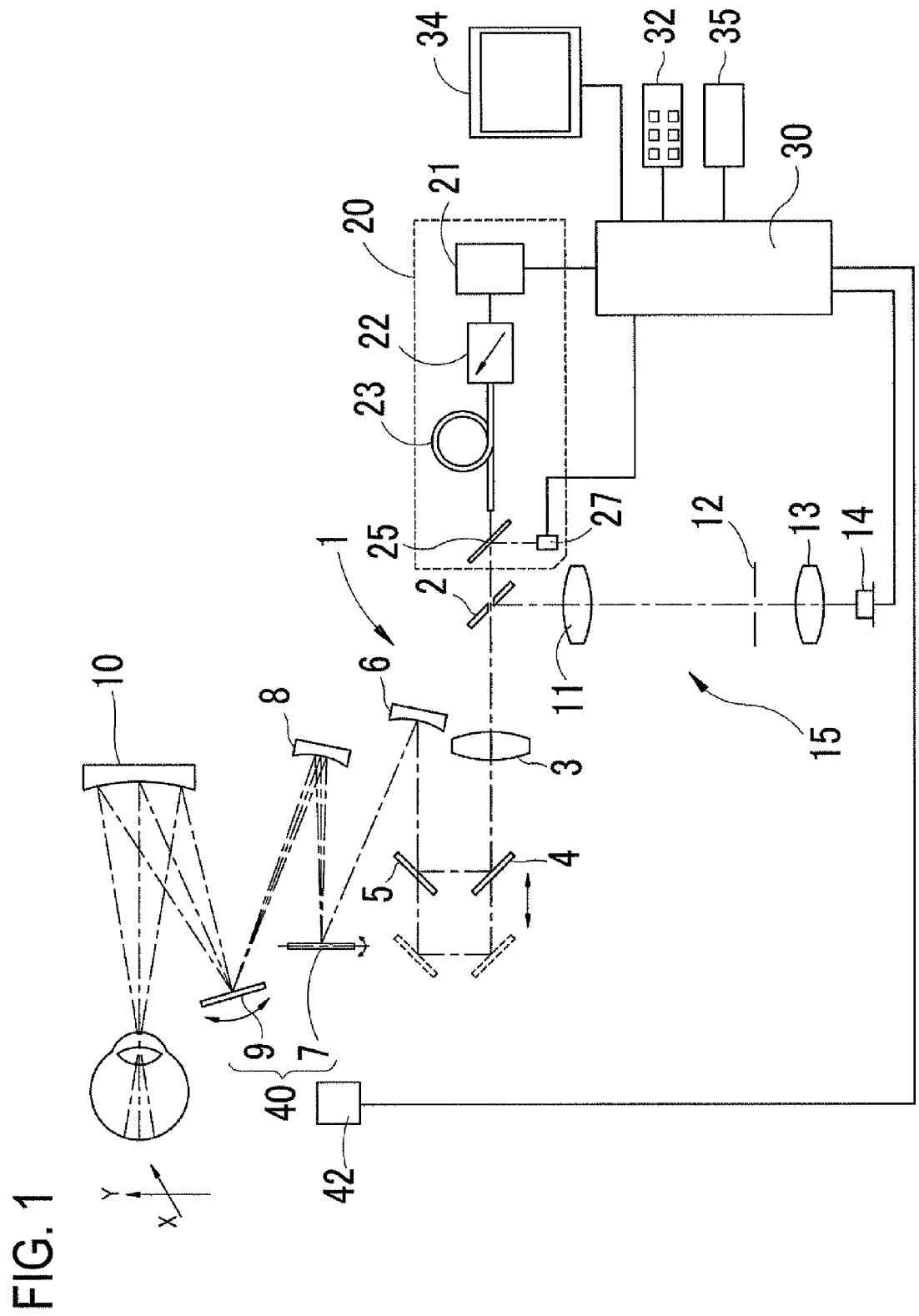
FIG. 1 is a schematic configuration view of an optical system and a control system of an ophthalmic imaging apparatus in an embodiment.

A detailed description of a preferred embodiment of the present invention will now be given referring to the accompanying drawings. FIG. 1 is a schematic configuration view of an optical system and a control system of an ophthalmic imaging apparatus in this embodiment. The following explanation is given to show an example of imaging a fundus as a predetermined portion of an examinee's eye. However, a subject to be imaged is not limited to the fundus.

An irradiation optical system 1 for irradiating a laser beam to the fundus of the examinee's eye includes a scanning optical system (a scanner) 40 for scanning a laser beam emitted from a laser emitter 20 on the fundus, and various types of optical components (a lens 3 to a concave mirror 10) for delivering the laser beam emitted from the laser emitter 20 to the fundus.

The laser beam emitted from the laser emitter 20 passes through an opening of a hole mirror 2 and the lens 3, and is reflected by flat mirrors 4 and 5, a concave mirror 6, a galvano mirror 7, a concave mirror 8, a galvano mirror 9, and a concave mirror 10 to irradiate the fundus. The flat mirrors 4 and 5 are moved in a direction indicated by an arrow in FIG. 1, thereby changing an optical path length of the laser beam to make focus adjustment (diopter correction).

The laser beam is moved on the fundus horizontally (in an X-axis direction) by the galvano mirror 7 and vertically (in a Y-axis direction) by the galvano mirror 9. Thus, the laser beam is made to scan on the fundus in two dimensions. The galvano mirrors 7 and 9 are driven by a drive part (the scanner) 42. As an alternative, a polygon mirror may be used instead of the galvano mirror 7. The scanning optical system 40 is not limited to the above mirror type and may adopt a wedge prism, an acousto-optical deflector (AOD), an electro-optical deflector (EOD), and others.

As the laser emitter 20, a laser emitter capable of emitting a laser beam with a tunable wavelength in a predetermined visible wavelength range is used. The laser emitter 20 includes an ultrashort pulse light source 21, a light intensity adjuster 22 connected to the pulse light source 21, and an optical fiber 23 connected to the adjuster 22. The adjuster 22 is connected to an arithmetic controller 30 to adjust the output of the pulse light source 21. The fiber 23 used in this embodiment is a polarization maintaining fiber having abnormal dispersion by wavelengths of excitation light.

Furthermore, the laser emitter 20 is provided with a dichroic mirror 25 that passes visible light and reflects infrared light and an infrared laser source 27 for observation. A laser beam emitted from the laser source 27 is reflected by the dichroic mirror 25 and passes through the components from the hole mirror 2 to the concave mirror 10 to irradiate the fundus.

When the output of the pulse light source 21 passes through the adjuster 22 and enters the fiber 23, a wavelength-tunable ultrashort pulse beam is generated by a nonlinear optical effect (herein, a soliton effect and a Raman scattering effect) in the fiber 23. A change amount (a shift amount) of the wavelength of the ultrashort pulse beam depends on the length of the fiber 23, the intensity of excitation light, and others. Thus, the change amount of the wavelength is controlled by adjusting those parameters. The wavelength is set so as to be tunable in a predetermined visible wavelength range (e.g., $\lambda$=380 nm to 760 nm). In this case, when a wavelength-tunable ultrashort soliton pulse has a short duration and high peak intensity, a third harmonic having one-third of the wavelength is generated by a third nonlinear optical effect. Using this, a visible-range wavelength is obtained.

A light-receiving optical system 15 for receiving the laser beam reflected by the fundus (a "fundus reflection beam") includes an apertured plate (e.g., a pinhole plate) 12 placed in a substantially conjugate position with a focal point of the laser beam on the fundus (in a substantially conjugate position with the fundus (the predetermined portion)), a light-receiving element 14 for receiving the laser beam having passed through the apertured plate 12, and various optical components (the concave mirror 10 to a lens 13) for delivering the fundus reflection beam to the light-receiving element 14.

The fundus reflection beam travels back along the aforementioned irradiation optical system 1 and is reflected by the hole mirror 2 placed in a substantially conjugate position with a pupil of the examinee's eye, and passes through a lens 11 to focus on the opening of the apertured plate 12. The fundus reflection beam having passed through the apertured plate 12 then passes through the lens 13 and is received by the light-receiving element 14.

The control system is explained below. The arithmetic controller 30 including an image processing part and others controls the entire apparatus. The arithmetic controller 30 is also connected with the pulse light source 21, the adjuster 22, the laser source 27, the light-receiving element 14, the drive part 42, a switch part 32, a monitor (a display) 34, a memory 35, and others. The arithmetic controller 30 forms a fundus image based on a light reception signal output from the light-receiving element 14. The monitor 34 displays the fundus image created in the arithmetic controller 30. In the switch part 32, various switches for setting various conditions of the apparatus are arranged. For example, there are an imaging start switch for outputting a trigger signal to start imaging, a focus switch for adjusting focus, and others.

Operations of the fundus imaging apparatus having the above configuration will be explained below. Upon power-on of the apparatus, the arithmetic controller 30 causes the laser source 27 to emit an infrared laser beam for observation to the fundus. An examiner makes alignment of the apparatus with respect to the examinee's eye by operating a joystick not shown or the like to move the apparatus so that the infrared laser beam is irradiated to the fundus and a desired fundus image appears on the monitor 34.

Figure 2:
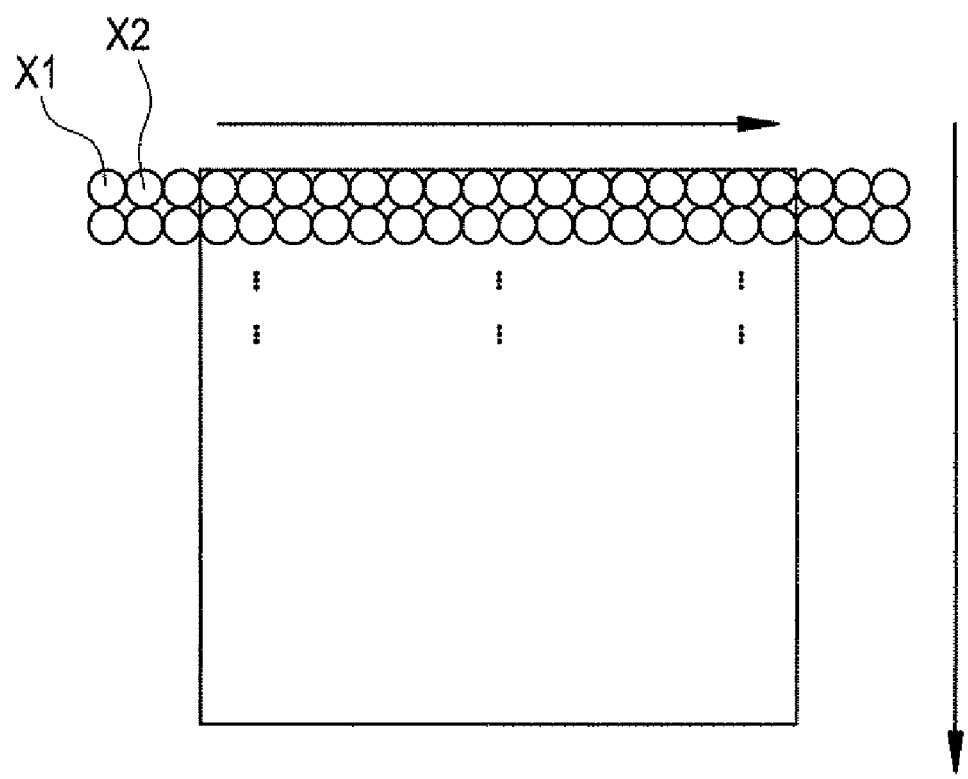
FIG. 2 is a diagram to explain scanning of a laser beam to obtain an image of one frame.

The arithmetic controller 30 sequentially arranges, as image data, the light reception signals from the light receiving element 14, obtained by the fundus reflection beam in a scanning range by the galvano mirrors 7 and 9, and displays them in a line in a lateral direction from the top of a display region of the monitor 34 (see FIG. 2).

Specifically, the arithmetic controller 30 holds the galvano mirror 9 at a predetermined angle and rotates the galvano mirror 7 in a predetermined direction within a predetermined scanning range, thereby acquiring the image data for one line. Then, the galvano mirror 9 is rotated by a predetermined angle, and the galvano mirror 7 is returned to a scanning-start reflection angle and then the galvano mirror 7 is rotated again in the predetermined direction. Thus, the image data for a next line is obtained. The image data for one line output from the light receiving element 14 is arranged in a row directly underneath the previously displayed image data of one line. When this processing is sequentially conducted, an imaging area of the fundus two-dimensionally scanned by the laser beam is obtained as one image (an image corresponding to one frame). When the image of one frame is obtained, the arithmetic controller 30 furthermore returns the galvano mirror 9 to a scanning-start reflection angle and controls the drive part 42 to scan the laser beam again from top down in a similar manner to the above.

The arithmetic controller 30 displays the thus obtained fundus image on the monitor 34. The examiner observes this fundus image and checks an alignment state, a focus state, and others with respect to the fundus (the imaging portion). When the fundus (the imaging portion) and the apparatus are in proper alignment, the examiner pushes the imaging start switch provided on the switch part 32.

Upon receipt of the trigger signal to start imaging, the arithmetic controller 30 starts acquisition of the hyperspectral image (or the multispectral image) using the laser emitter 20. The arithmetic controller 30 controls the adjuster 22 to continuously change the central wavelength of the laser beam in a predetermined visible wavelength range and controls the drive part 42 in association with changing of the wavelength of the laser beam emitted from the laser emitter 20 and also two-dimensionally changes or moves an irradiation position of the laser beam. The arithmetic controller 30 obtains a light reception signal including spectral data at each irradiation position (a focal point) from the light receiving element 14.

Figure 3:
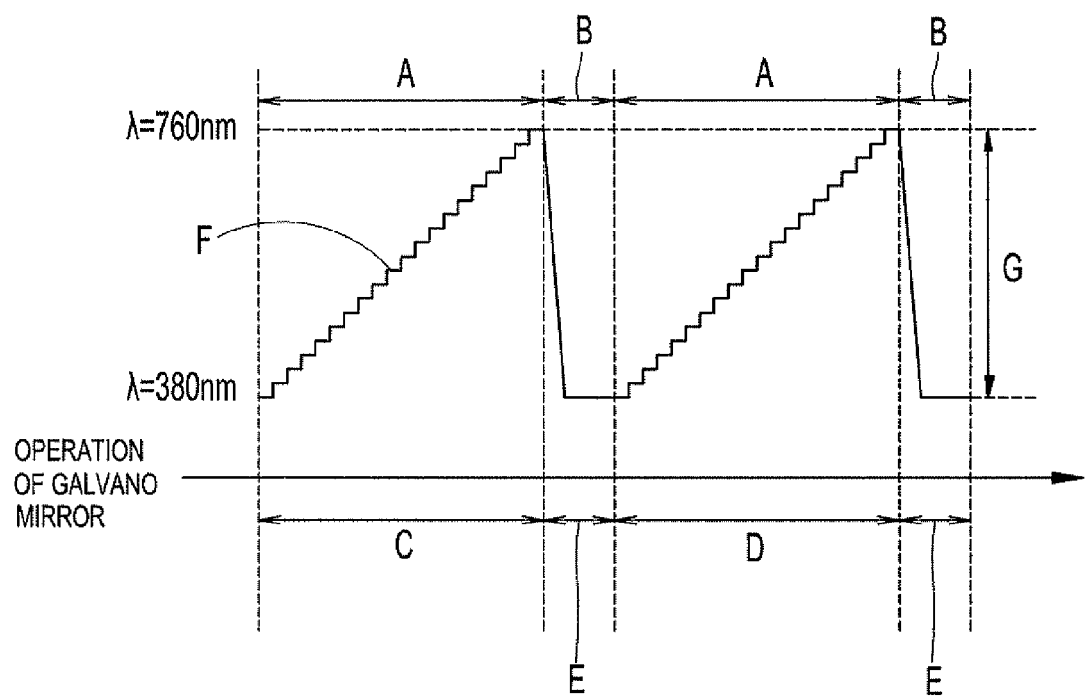
FIG. 3 is a graph showing a concrete example of operations for obtaining spectral data at each irradiation position of a laser beam.

FIG. 3 is a graph showing a concrete example of operations for obtaining the spectral data at each irradiation position. The arithmetic controller 30 synchronizes changing of the wavelength and changing of the irradiation position so that the spectral data in the predetermined visible wavelength range is detected by the light receiving element 14 at each irradiation position (the focal point) of the laser beam on the fundus. In this case, for instance, the arithmetic controller 30 changes wavelengths according to the time (frequency) for which the angle of the mirror 7 is changed by a predetermined amount (angle) to change the irradiation position.

When a first irradiation position X1 is set by the drive part 42, the arithmetic controller 30 changes the intensity of excitation light with time by use of the adjuster 22, thereby changing the wavelength of the laser beam emitted from the laser emitter 20 to another one in the predetermined visible wavelength range. The arithmetic controller 30 continuously (or stepwise) changes the intensity of excitation light to continuously change the wavelength of the laser beam, thereby obtaining continuous spectral data in the predetermined visible wavelength range.

In this case, for obtaining such continuous spectral data, it is preferable to change the wavelength of the laser beam in steps of 10 to 20 nm in the predetermined visible wavelength range. Furthermore, the wavelength of the laser beam is changed (shifted) in the step corresponding to a half-bandwidth (e.g., about 20 nm) of the laser beam. Thus, continuous spectral data can be obtained effectively.

As above, when the wavelength of the laser beam emitted from the laser emitter 20 is changed, the corresponding fundus reflection beam is received successively by the light receiving element 14. In this case, the light reception signals output from the light receiving element 14 are associated with the wavelengths of the laser beam and obtained as spectral data. Since the light reception signals output from the light receiving element 14 are associated with wavelength change data by the adjuster 22, a light reception signal for each wavelength is obtained.

When the spectral data at the first irradiation position X1 is obtained, the arithmetic controller 30 controls the drive part 42 to set the irradiation position of the laser beam to a second irradiation position X2. The arithmetic controller 30 changes the wavelength of the laser beam in a similar manner to the case of the first irradiation position X1 and obtains spectral data at the second irradiation position X2. In this way, the arithmetic controller 30 controls the laser emitter 20 and the drive part 42 to obtain the spectral data at each pixel position of the fundus image. Each irradiation position can be regarded as corresponding to one pixel for forming a two-dimensional fundus image. Accordingly, the arithmetic controller 30 has only to cause the laser beam emitted from the laser emitter 20 to two-dimensionally scan so as to obtain the spectral data per predetermined pixel.

The configuration of obtaining the spectral data at each irradiation position includes not only obtaining the spectral data while the mirror angle is fixed to fix the irradiation position but also obtaining the spectral data in a predetermined minute region while the mirror angle is changed at a predetermined speed (for example, during use of a polygon mirror).

The arithmetic controller 30 stores the spectral data obtained at each irradiation position in the memory 35 by associating the data with each pixel position in the two-dimensional fundus image. Accordingly, a hyperspectral image of the fundus including the spectral data per pixel is obtained. As an alternative, it may also be arranged to obtain image data per wavelength based on the obtained spectral data and store the fundus image per wavelength in the memory 35.

Then, the arithmetic controller 30 displays the fundus image on the monitor 34 based on the hyperspectral image stored in the memory 35. In this case, based on the hyperspectral image stored in the memory 35, the arithmetic controller 30 synthesizes, per pixel, light reception signals of at least two or more wavelengths among the light reception signals associated with corresponding wavelengths, and displays the synthesized image on the monitor 34. For instance, the arithmetic controller 30 may continuously synthesize the light receipt signals associated with the wavelengths in relation to a predetermined visible wavelength range and display a color fundus image continuously covering the predetermined visible wavelength range on the monitor 34. Another alternative is to display a fundus image obtained by synthesizing images (at least two wavelengths) based on light receipt signals of any different wavelengths from each other. Furthermore, another alternative is to make various analyses on the obtained fundus image and display an analysis result thereof on the monitor 34.

With the above configuration, it is possible to obtain the hyperspectral image of the fundus as a confocal image, so that a high-resolution fundus image having spectral data of various wavelengths can be obtained. In this case, more information can be obtained than the fundus image obtained by use of the red, green, blue monochromatic laser sources. This therefore enables accurate analysis.

Since the data per wavelength are synthesized and the fundus image based on the hyperspectral image is displayed on the monitor 34, a color fundus image can be expressed in more accurate color. In this case, the state of the fundus can be more precisely expressed than the synthesized image of the fundus images produced by the red, green, and blue monochromatic lasers.

In the above configuration, the hyperspectral image of the fundus is obtained by continuously changing the wavelength per one pixel. An alternative is to sequentially change the wavelength according to a frame rate at which a fundus image is to be obtained. In this case, the arithmetic controller 30 sets the laser beam from the laser emitter 20 at a first wavelength and controls the drive part 42 to obtain the fundus image based on the light reception signals corresponding to the first wavelength. Then, the arithmetic controller 30 sets the laser beam from the laser emitter 20 at a second wavelength and obtains the fundus image based on the light reception signals corresponding to the second wavelength. By continuously changing the wavelength every time one fundus image is obtained in this way, the hyperspectral image is obtained.

It is preferable to obtain the spectral data in a wide wavelength range and at small wavelength intervals. However, any configuration that can produce an image based on the spectral data corresponding to intermediate colors existing between red, green, and blue can also show effects at a fixed level.

In the above configuration, the infrared laser source 27 is provided separately from the wavelength-tunable laser emitter 20. Another configuration may be adopted in which a wavelength-tunable laser emitter 20 capable of emitting a laser beam with a wavelength tunable from a predetermined visible wavelength range to a predetermined infrared wavelength range and the infrared laser source 27 is not provided. In this case, the arithmetic controller 30 controls to change the wavelength so that an infrared laser beam is irradiated to the fundus when an observation mode is selected and a visible laser beam is irradiated to the fundus when a spectral image obtaining mode is selected.

Another possible configuration is to include a second ultrashort pulse laser source and a second laser emitter for emitting a laser beam with a tunable wavelength in a predetermined infrared wavelength range, and control the second laser emitter to obtain a hyperspectral image or a multispectral image. The arithmetic controller 30 controls the second laser emitter to continuously change a central wavelength of the laser beam in a predetermined infrared wavelength range as with the visible laser beam from the laser emitter 20, and controls the scanner in association with wavelength changes of the laser beam to change a irradiation position of the laser beam two-dimensionally.

While the presently preferred embodiment of the present invention has been shown and described, it is to be understood that this disclosure is for the purpose of illustration and that various changes and modifications may be made without departing from the scope of the invention as set forth in the appended claims.

The invention claimed is:

1. An ophthalmic imaging apparatus comprising:
    a laser emitter that includes an ultrashort pulse light source and emits a laser beam with a tunable wavelength in a predetermined visible wavelength range;
    an irradiation optical system that includes a scanner for scanning the laser beam two-dimensionally and irradiates the laser beam emitted from the laser emitter to a predetermined portion of an examinee's eye;
    a light receiving optical system including an apertured plate placed in a substantially conjugate position of a focal point of the laser beam on the predetermined portion and a light receiving element for receiving the laser beam reflected by the predetermined portion and passed through the apertured plate;

a controller that controls the laser emitter to continuously change a central wavelength of the laser beam in a predetermined visible wavelength range and controls the scanner in association with the wavelength change of the laser beam to two-dimensionally change an irradiation position of the laser beam;

a memory that stores a light reception signal of the light receiving element associated with the wavelength change of the laser beam and the irradiation position change of the laser beam; and a display, the controller being adapted to display an image of the predetermined portion on the display based on the light reception signal stored in the memory.

2. The ophthalmic imaging apparatus according to claim 1, wherein the controller controls the laser emitter to continuously change the wavelength of the laser beam per irradiation position of the laser beam.

3. The ophthalmic imaging apparatus according to claim 1, wherein the controller controls the laser emitter to sequentially change the wavelength of the laser beam according to a frame rate at which an image is obtained.

4. The ophthalmic imaging apparatus according to claim 1, wherein the controller displays an image based on the light reception signal associated with at least two or more wavelengths.

5. The ophthalmic imaging apparatus according to claim 1, further comprising a second laser emitter that includes a second ultrashort pulse light source and emits a laser beam with a tunable wavelength in a predetermined infrared wavelength range, and the controller being adapted to control the second emitter to continuously change a central wavelength of the laser beam in a predetermined infrared wavelength range and control the scanner in association with the wavelength change of the laser beam to two-dimensionally change an irradiation position of the laser beam.

* * * * *